United States Patent
Sieckmann et al.

(10) Patent No.: US 9,217,694 B2
(45) Date of Patent: Dec. 22, 2015

(54) METHOD FOR AUTOMATICALLY GENERATING LASER CUTTING LINES IN LASER MICRODISSECTION PROCESSES

(75) Inventors: Frank Sieckmann, Bochum (DE); Gerhard Johannsen, Wettenberg (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 2482 days.

(21) Appl. No.: 10/576,453

(22) PCT Filed: Oct. 21, 2004

(86) PCT No.: PCT/EP2004/052600
§ 371 (c)(1),
(2), (4) Date: Apr. 20, 2006

(87) PCT Pub. No.: WO2005/040762
PCT Pub. Date: May 6, 2005

(65) Prior Publication Data
US 2007/0066967 A1    Mar. 22, 2007

(30) Foreign Application Priority Data

Oct. 21, 2003  (DE) .................................. 103 49 411
Oct. 21, 2004  (DE) .......................... 10 2004 051 508

(51) Int. Cl.
*B23K 26/00* (2006.01)
*B23K 26/16* (2006.01)
(Continued)

(52) U.S. Cl.
CPC .............. *G01N 1/2813* (2013.01); *G02B 21/32* (2013.01); *G02B 21/365* (2013.01); *G01N 2001/288* (2013.01)

(58) Field of Classification Search
CPC ............. B23K 26/032; B23K 26/0024; B23K 26/0656; G01N 1/286; G01N 1/31; G01N 1/30; G01N 1/06; G01N 1/04; G01N 1/2806; G01N 1/2813; G01N 1/44; G01N 1/34; G01N 2001/288; G02B 21/32; G02B 21/365
USPC ............... 219/121.7, 121.67, 121.72, 121.68, 219/121.73, 6; 435/4, 50, 6, 173.7, 173.1, 435/173.9, 40.2, 40.5; 83/13; 600/564; 356/36; 606/10, 13
See application file for complete search history.

(56) References Cited

U.S. PATENT DOCUMENTS

| 4,538,299 A | 8/1985 | DeForest |
| 4,741,043 A | 4/1988 | Bacus ............................... 382/6 |

(Continued)

FOREIGN PATENT DOCUMENTS

| DE | 38 36 716 | 5/1990 |
| DE | 42 11 904 | 11/1992 |

(Continued)

OTHER PUBLICATIONS

International Search Report for PCT/EP2004/052600 (4 pages).
(Continued)

*Primary Examiner* — Hung D Nguyen
(74) *Attorney, Agent, or Firm* — Leydig, Voit & Mayer, Ltd.

(57) ABSTRACT

A laser microdissection method includes capturing an electronic image of an image detail of a specimen. The image detail is processed using image analysis so as to automatically ascertain an object to be cut out. A nominal cutting line around the object to be cut out is automatically defined. Subsequently, the object is cut out in response to a relative motion between a laser beam and the specimen.

26 Claims, 7 Drawing Sheets

(51) Int. Cl.
*A61B 18/16* (2006.01)
*G01N 1/28* (2006.01)
*G02B 21/32* (2006.01)
*G02B 21/36* (2006.01)

(56) References Cited

U.S. PATENT DOCUMENTS

| | | | | |
|---|---|---|---|---|
| 5,031,099 | A | 7/1991 | Kettler | 364/413.08 |
| 5,843,644 | A | 12/1998 | Liotta et al. | 435/6 |
| 5,843,657 | A | 12/1998 | Liotta et al. | 435/6 |
| 5,998,129 | A | 12/1999 | Schütze et al. | 435/4 |
| 6,316,234 | B1 * | 11/2001 | Bova | 435/173.7 |
| 6,377,710 | B1 * | 4/2002 | Saund | 382/258 |
| 6,713,264 | B2 | 3/2004 | Luttermann et al. | 435/7.1 |
| 6,787,301 | B2 | 9/2004 | Ganser et al. | 435/4 |
| 6,907,798 | B2 | 6/2005 | Ganser et al. | 73/864.41 |
| 6,991,714 | B1 | 1/2006 | Gauss et al. | 204/462 |
| 2001/0053245 | A1 * | 12/2001 | Sakai et al. | 382/151 |
| 2002/0025511 | A1 * | 2/2002 | Bova | 435/4 |
| 2002/0048747 | A1 * | 4/2002 | Ganser | 435/4 |
| 2002/0090122 | A1 | 7/2002 | Baer et al. | 382/128 |
| 2002/0164678 | A1 | 11/2002 | Ganser et al. | 435/40.5 |
| 2004/0252291 | A1 * | 12/2004 | Schutze | 356/36 |

FOREIGN PATENT DOCUMENTS

| | | | |
|---|---|---|---|
| DE | 196 36 074 | 3/1998 | |
| DE | 19636074 A1 * | 3/1998 | G06K 9/66 |
| DE | 196 29 141 | 4/1998 | |
| DE | 198 15 400 | 10/1999 | |
| DE | 695 10 925 | 2/2000 | |
| DE | 100 18 251 | 10/2001 | |
| DE | 100 43 506 | 12/2001 | |
| JP | H0571991 B2 | 10/1993 | |
| JP | 2000231640 A | 8/2000 | |
| WO | 9609594 A1 | 3/1996 | |
| WO | 0133190 A2 | 5/2001 | |
| WO | WO 01/73398 | 10/2001 | |
| WO | WO 03036266 A1 * | 5/2003 | G01N 1/28 |

OTHER PUBLICATIONS

P.A.L.M. Microlaser Technologies: PALM MicroBeam IP-MS + Metafer P, Feb. 2003 (4 pages).
Arcturus: "Laser Capture Microdissection (LCM) Systems", XP-002315059 (6 pages).
B. J. Schachter et al.: "Some Experiments in Image Segmentation by Clustering of Local Feature Values", XP-002269476, Pattern Recognition, vol. 11, Pattern Recognition Society, Pergamon Press Ltd., Great Britain, pp. 19-28.
H. Rohling "Einführung in die Informations- und Codierungstheorie", Teubner Publishers, Feb. 1995, pp. 1-15.
J. Sierra Image Analysis and Mathematical Morphology, Academic Press, Dec. 1998.
Schnaider, Mustererkennung, http://www.zgdv.de/zgdv/departments/z2/Z2Staff/scheide/localimages/ME2003-02.pdf, Apr. 8-Aug. 8, 2003.
Schuetze et al., Laser-Bio-Dynamik, Nov. 21, 2002, Messe MEDICA 2002, pp. 108-115.
Prospekt Neue lasergestützte Verfahren in der Medizin und Biologie, Prospekt zu einer Abschlussprsentation Laser-Bio.Dynamik, Nov. 21, 2002, Messe MEDICA 2002.
Saegmueller, Information zum Systemdesign des Gerätes MicroBeam IP-MS, Palm Microlaser Technologies AG, Aug. 21, 2002.

* cited by examiner

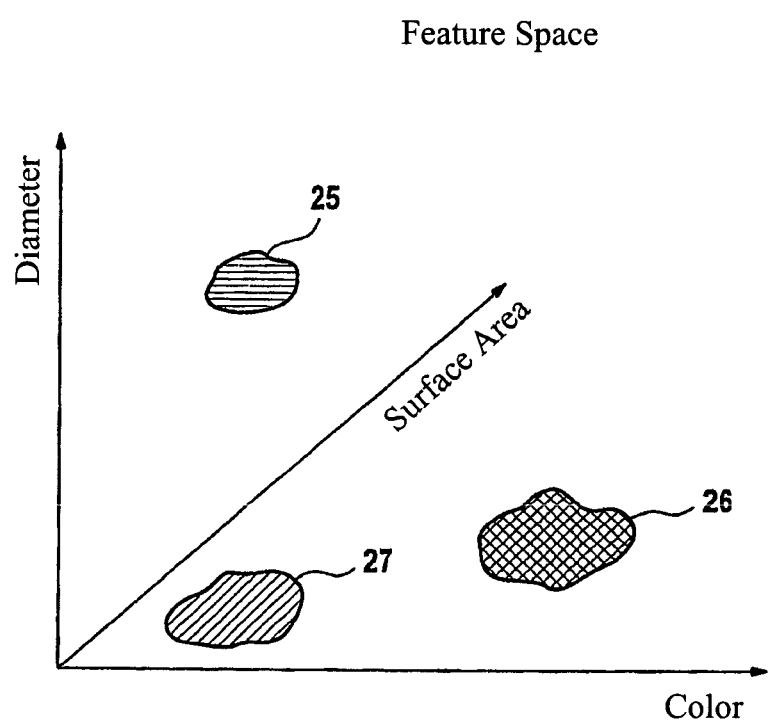
Fig. 1.1

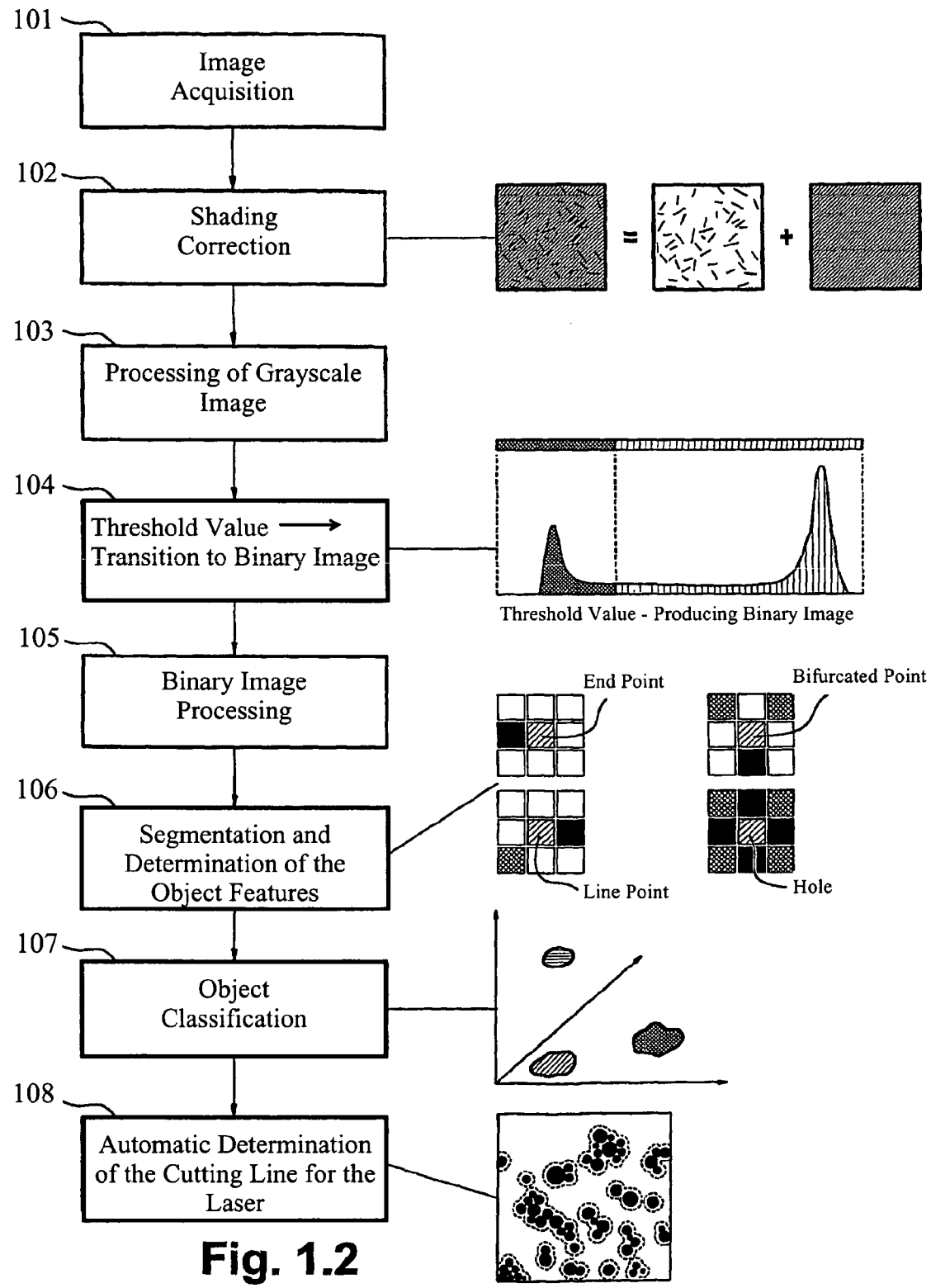
Fig. 1.2

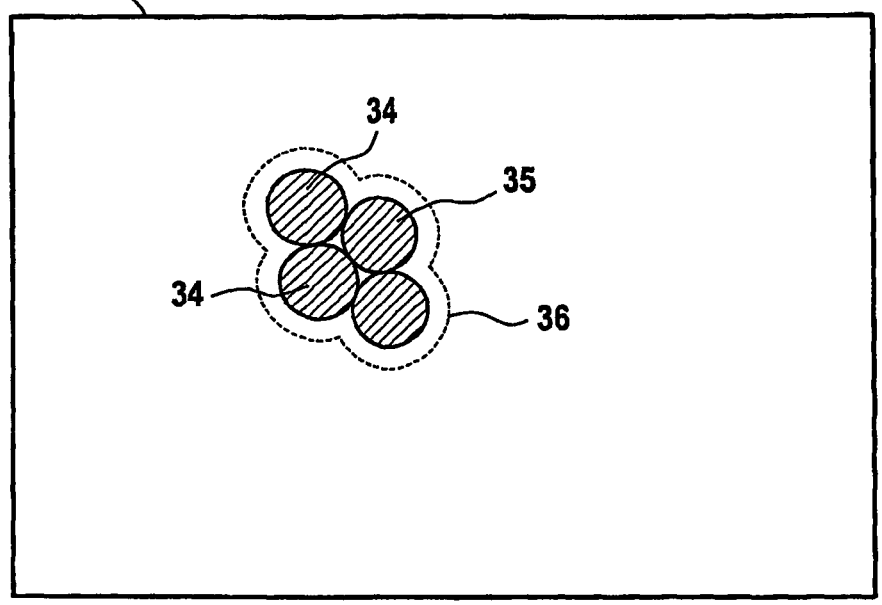
Fig. 1.3
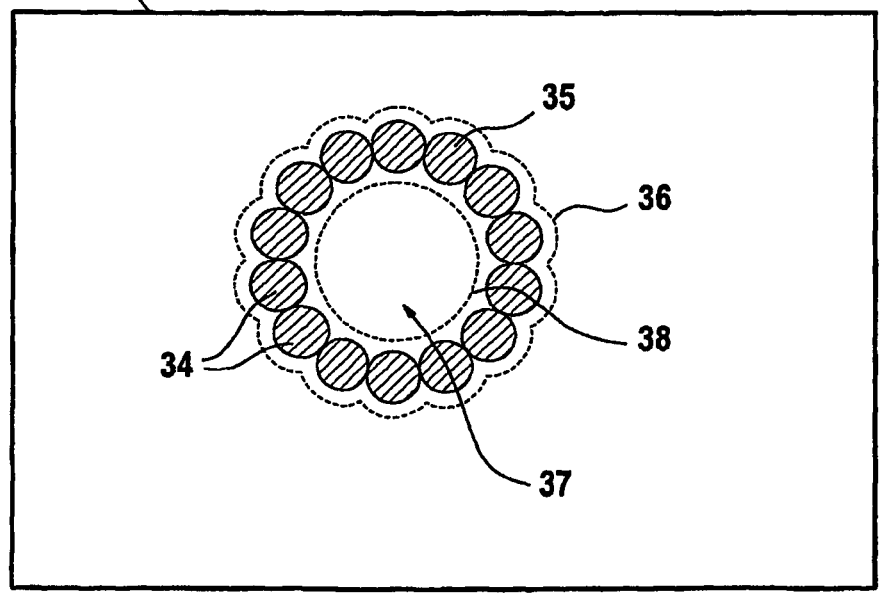
Fig. 1.4

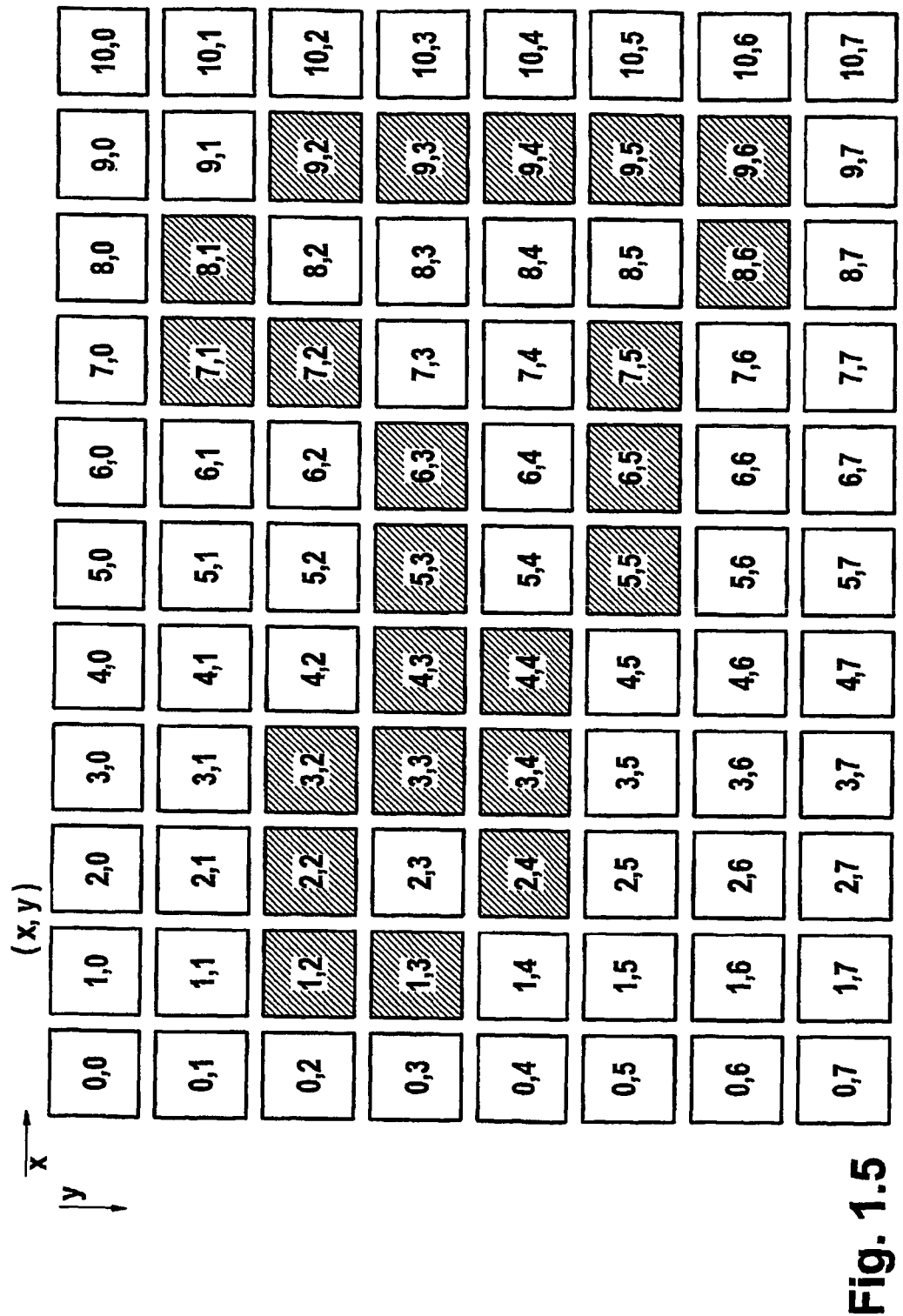
Fig. 1.5

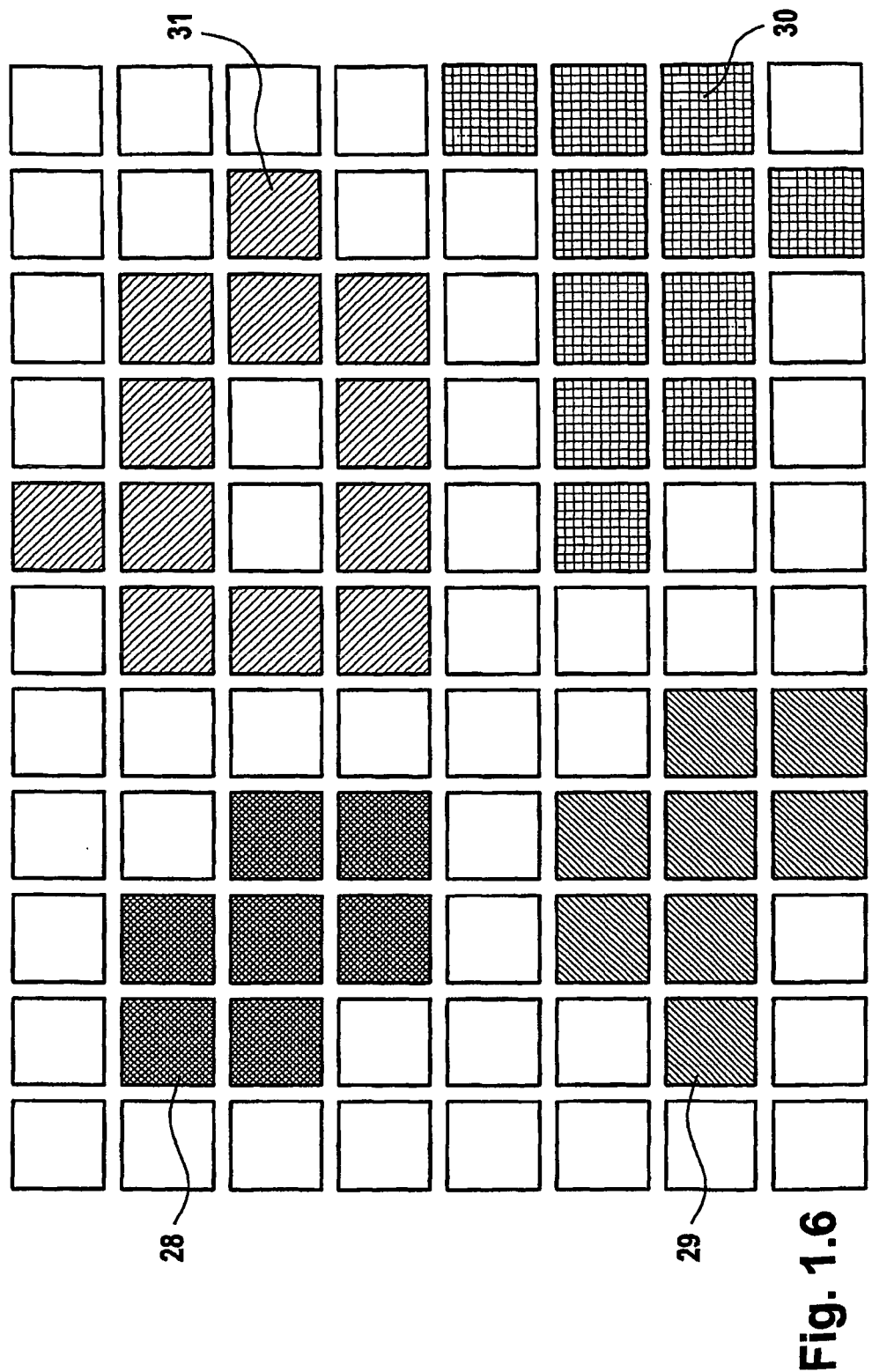
Fig. 1.6

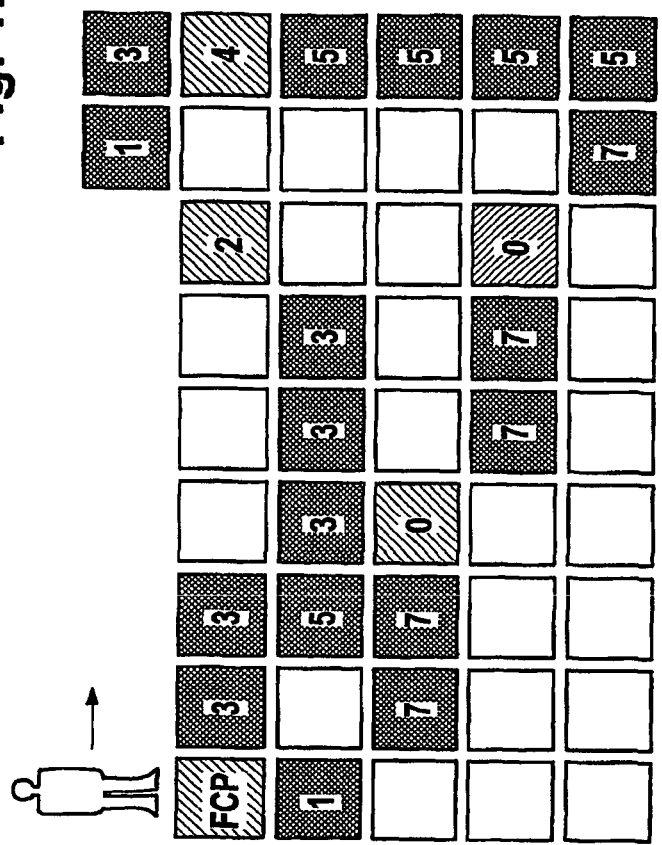
Fig. 1.7
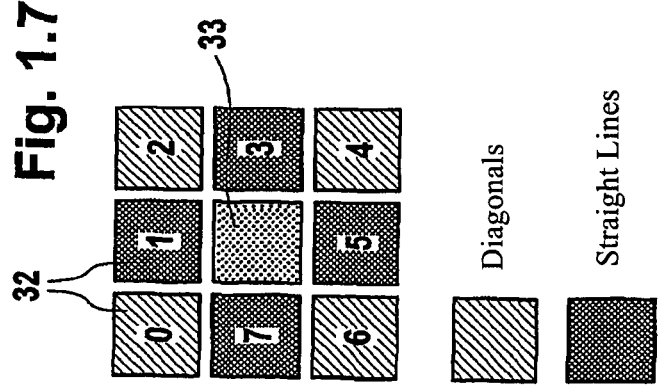
Fig. 1.7a
Fig. 1.7b
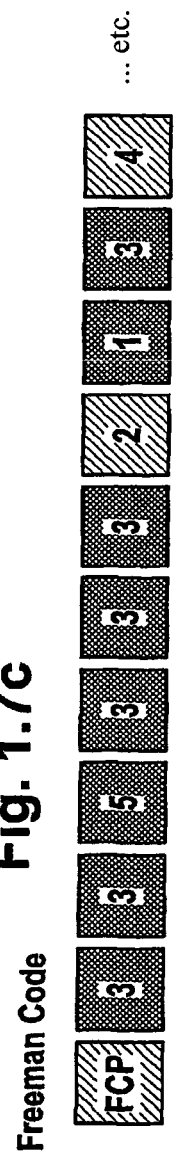
Fig. 1.7c

METHOD FOR AUTOMATICALLY GENERATING LASER CUTTING LINES IN LASER MICRODISSECTION PROCESSES

The present invention relates to a laser microdissection method in which a nominal cutting line is marked for an object to be cut out from a microscopic specimen, and the object is subsequently cut out in response to a relative motion between a laser beam and the specimen.

BACKGROUND

Laser microdissection systems are used for extracting selected microscopic objects from biological specimens using a laser beam produced by a laser. The material (the collected microdissected pieces) extracted in sufficient quantities is subsequently supplied to further biochemical analysis steps. At present, laser microdissection systems are predominantly used in the medico-biological field.

A laser microdissection method and a laser microdissection system of this kind are described, for example, in German Patents No. DE 100 43 506 C1 and DE 100 18 251 C2. Such a laser microdissection system is made up of a plurality of precisely mutually synchronized components. The central component is a microscope which has many motorized functions and which includes an electronically adjustable x-y stage for accommodating the specimen to be processed. The laser beam produced in a laser unit is coupled via an optical system having integrated beam deflection into the beam path of the microscope and is deflected by the microscope objective onto different locations of the fixed specimen in order to cut the same. In another embodiment, the laser beam is held immovably, and the specimen is moved by the x-y stage relative thereto. All of the control functions are executed by a suitably designed program which runs on a connected computer. The image detail of the specimen that is visible in the microscope is displayed on the computer monitor by a camera that is adapted to the microscope. Using the computer mouse, the user can draw a boundary line, referred to in the following as a nominal cutting line, around selected specimen regions, enclosing the same. Every line drawn in this manner is characterized by a series of x-y point coordinates which are defined relative to the monitor coordinates. Upon activation of the cutting command, the laser beam is controlled by a suitable x-y mapping system in such a way that the previously defined drawing line is imaged onto the specimen, so that a true-to-scale, affine mapping of the monitor line is scanned on the specimen. Thus, the objects that had been manually marked beforehand are cut out by the properly adjusted laser beam. As described in German Patent No. DE 100 18 251 C2, the system allows the microdissected pieces to be selectively collected for further processing in a standardized small collection vessel underneath the cutting plane, a plurality of collection vessels being selectable and automatically movable to the collecting position.

However, the inherent drawback of the known laser microdissection method is that the process of marking the objects to be cut out, as undertaken by the user, is complex, time-consuming, and error-prone. This holds true in particular when a relatively large number of microdissected pieces is required for the subsequent analysis steps. In this case, fatigue and other influences affecting the user can have serious consequences.

SUMMARY OF THE INVENTION

It is, therefore, an object of the present invention to provide a laser microdissection method which will permit a high specimen throughput in a largely error-free process.

The present invention provides a laser microdissection method in which a nominal cutting line is marked for an object to be cut out from a microscopic specimen, and the object is subsequently cut out in response to a relative motion between a laser beam and the specimen. In the method, an electronic image (grayscale image or color image) of at least one image detail of the specimen is captured. Image analysis is subsequently used to process the image detail and to determine the object to be cut out. The nominal cutting line around the object to be cut out is subsequently automatically defined. In response to a user command, the object may then be cut out along the nominal cutting line by a laser beam.

One advantageous embodiment of the method provides for control signals for controlling a relative motion between the laser beam and the specimen to be derived from the automatically defined nominal cutting line in a likewise automatic additional method step. The laser cutting line is then produced automatically, without intervention by the user.

The present invention overcomes the mentioned disadvantages through the consistent application of image analysis methods and by providing a substantially enhanced level of microscope automation. The automation primarily involves positioning the specimen region to be examined over the electronically adjustable stage.

To achieve an especially high level of automation and a marked increase in the sample throughput, another embodiment of the method provides for a so-called meander function to be defined in the associated application program, to ensure that the stage containing the specimen is properly advanced during routine operation. In the process, the specimen is automatically scanned in a meander form, image field by image field, so that the entire specimen region selected by the user is incrementally captured by the camera. On the one hand, the boundaries of the specimen region of interest, as well as the magnification of the microscope objective which sets the size of the image field, may be defined in the system's setting mode. On the other hand, the type and settings of a focusing system, with whose assistance the requisite focus setting is provided for the images to be processed during the automatic transverse feed motion of the stage, may be defined. In conjunction with the meander function, this method permits a fully automatic processing of the specimen, without requiring any intervention by the user.

Each time a new specimen position is automatically reached, an image is recorded by the camera. Using image analysis methods, each recorded image is then examined to determine whether it contains objects whose characteristic features conform with previously programmed-in features, the degree of conformity being settable. If there is sufficient conformity, the object is recognized and marked. For all recognized objects, one single and closed boundary line is produced by performing an automatic contour calculation. A matrix transformation is applied to "dilate" this boundary line, while preserving its shape, with the result that it surrounds the object at a greater clearance distance than the nominal cutting line. This procedure makes it possible to allow for the final cut thickness of the laser beam. Every nominal cutting line obtained in this manner is characterized by a series of x-y point coordinates which are defined relative to the monitor coordinates. By following an appropriate x-y mapping instruction, a true-to-scale, affine mapping of the cutting line is generated that is required for proper deflection of the laser beam.

Once the image at hand is processed in the manner described, the automatic transverse feed motion of the stage positions the specimen at the next image field, where it is analyzed. A selectable collection vessel is automatically moved to the collection position. This procedure is repeated until the defined specimen region has been processed or a previously set number of objects has been cut out. Following the cutting operation, each cut-out object leaves behind a hole in the specimen, precisely at the time of successful completion of the cutting procedure. The hole essentially corresponds to the surface area of the previously detected object (within the contour line), without the expansion resulting from the thickness of the laser cut.

For that reason, comparing the surface area of the cut-out hole detected by image analysis with the surface area of the previously detected object is an effective way for making a binary assessment of the cut.

The advantage of the method according to the present invention is that, once properly adjusted, the system works without further monitoring by a user. Thus, the indicated method leads to a markedly increased sample throughput, while simultaneously enhancing ruggedness and reliability. Since the feature data records, once verified, may be stored, this leads to absolutely reproducible conditions when substantially similar specimen are used. In statistical measurements, in particular, this reproducibility is an absolute prerequisite for a good confidence range of the results.

In addition, by employing a plurality of feature data records, different object types within one specimen may be recognized and cut out in one sequence of operation. Since one may select among a plurality of vessels for collecting the microdissected pieces underneath the cutting plane, different object types are also able to be collected in different vessels.

The system may, of course also distribute or read in the feature data records via a database server and/or any given network (LAN=local area network, WLAN=wireless local area network (radio network), Bluetooth, TCP/IP, Internet), but also via any given media in printed or electronic form. This makes it possible for a plurality of laser microdissection systems to be synchronized within one interconnected network. Particularly when working with large numbers of statistically predefined test quantities that require processing under time pressure, this objective may be achieved by clustering and synchronizing a plurality of laser microdissection systems via one network using coordinated feature data records.

BRIEF DESCRIPTION OF THE DRAWINGS

The present invention is described in greater detail in the following based on exemplary embodiments with reference to the schematic drawings, which show:

FIG. 1.1: a feature space for classifying the objects;
FIG. 1.2: a flow chart of the process sequence;
FIG. 1.3: the combining of objects into so-called clusters;
FIG. 1.4: a cluster having an interior hole;
FIG. 1.5: an image detail including a binary object;
FIG. 1.6: four objects labeled with different grayscale values;
FIG. 1.7: Freeman code and object including encoding of the boundary pixels, wherein FIG. 1.7a shows an eight-pixel neighborhood for a Freeman code, FIG. 1.7b shows boundary pixels of an object and 1.7c shows the corresponding notation of the Freeman code for the boundary pixels of the object shown in FIG. 1.7b.

Figure 2:
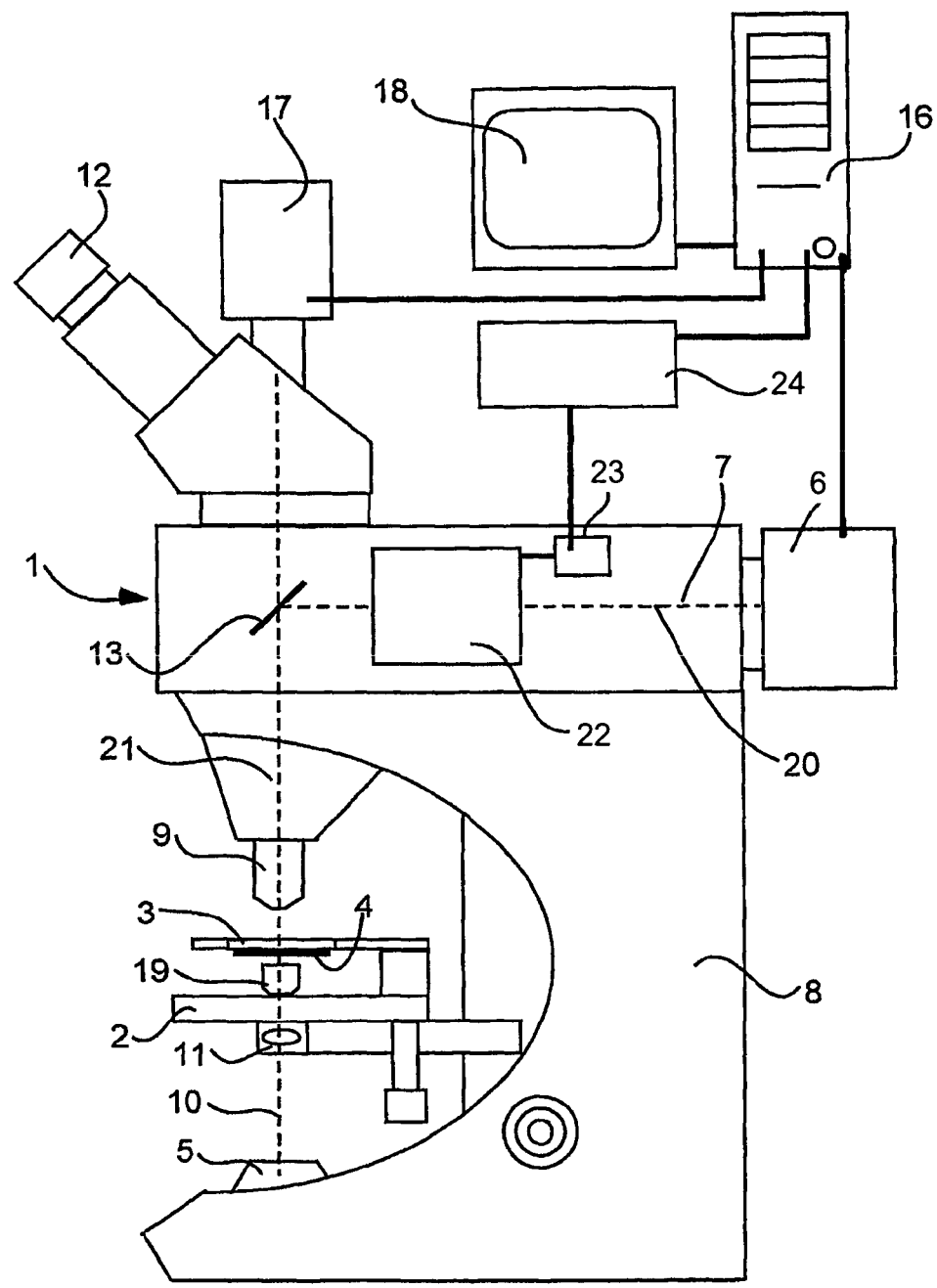
FIG. 2: a laser microdissection device for implementing the method.

Image analysis methods can be employed to automatically classify objects within an image. Analyses supported by image analysis are typically based on a feature analysis. In this procedure, one makes use of the fact that every object can be recognized and classified by a certain number of individual features. Features can include variables such as surface area, perimeter, diameter, mass, texture, color, shape, etc., for example. By selecting a suitable set of features, an object can be classified and differentiated from other objects.

Typically, this suitable set of features is plotted in an n-dimensional feature space. In FIG. 1.1, a feature space having the features color, surface area, and diameter is selected exemplarily. Objects having "little" color, a small diameter and a small surface area are then classified, for example, by feature cluster 27, which describes an "object 3." On the other hand, "object 2", which is represented by feature cluster 26, is differentiated by its abundance of color, small diameter, as well as small surface area. However, "object 1", which is described by feature cluster 25, has little color, a large diameter, as well as a large surface area. Thus, in accordance with FIG. 1.1, we may differentiate among three objects.

TABLE 1.1

(Example) Object Classification by Object Features

| | Color | Periphery (μm) | Surface area (μm$^2$) |
| --- | --- | --- | --- |
| object 1 | little | large | large |
| object 2 | great deal | small | small |
| object 3 | little | small | small |

The situation can arise that the feature regions of two objects overlap, precluding the features from being uniquely assigned to the one or the other object. In such a case, new features may be added to obtain a unique assignment.

Object features may be ascertained by performing image analysis calculations. The complete functional sequence, including the determination of the object features, may be broken down into different incremental steps. The flow chart illustrating one advantageous embodiment of the method is presented in FIG. 1.2. It includes the following steps 101 through 108.

Step 101: Image acquisition:
The image is first acquired using a suitable device, for example a microscope having an adapted camera; the camera may be an analog or a digital camera. Depending on the type of objects to be classified, a color or a grayscale camera may be used.

Step 102: Shading Correction:
Shading correction may then be automatically applied to this image; i.e., this step is optional. This process takes into account that the image quality is already distorted by the illumination due to an inhomogeneous illumination of the image field. This problem is overcome in the present case by the automatic use of a shading image which is automatically or manually captured beforehand and stored. In the process, the specimen slide stage is moved to a so-called empty position which is characterized in that, at this location, the system is able to acquire an undistorted image of the illumination distribution by using an empty specimen slide. This image is undistorted since there is no biological material on the specimen slide between the objective and the illumination source. This correction image is then applied later to all images captured under the same optical conditions, in order to automatically correct the shading influence caused by the inhomogeneity of the specimen illumination.

Step 103: Grayscale Image Processing:
In accordance with the schematic representation in FIG. 1.2, the "grayscale value processing" follows at this point. The shading correction referred to above may also already be understood to be grayscale value processing. In this step, minor artifacts in the image are first removed using grayscale morphology.

Step 104: Threshold Value and Transition to the Binary Image:
Various image analysis methods are known for threshold value determination. To obtain a most rugged method possible, the optimal threshold value for the transition from the grayscale image to the binary image, usually referred to as segmentation, may preferably be ascertained using a so-called entropy maximization approach. The idea underlying entropy maximization is for a threshold value to be determined in the grayscale value histogram of the image in such a way that the binary image derived by applying this threshold value exhibits a maximum possible entropy. As is known, for example, from H. Rohling, "Einführung in die Informations—und Codierungstheorie" [*An Introduction to Information and Encoding Theory*], Teubner Publishers 1995, the entropy content is a measure of the information content of an image. Thus, by determining the threshold value using the entropy maximization approach, a binary image is obtained having a maximum possible information content.

This method is well suited for automatic segmentation, thus for automatically extracting image objects from an image. Segmentation processes are described in detail in books on the fundamentals of image processing, for example in the book by Sierra, J., "Image Analysis and Mathematical Morphology", Academic Press, 1988.

In the method presented, the segmentation of image objects is a prerequisite for computing the laser cutting line, i.e., the line along which the laser is directed during the laser microdissection process. When working with image objects that are not easily segmented, the user may additionally manually specify a threshold value for producing binary images, by defining a separate threshold value for each color channel.

Step 105: Binary Image Processing:
In accordance with FIG. 1.2, the binary image processing follows at this point as a further step. In this case, minor artifacts (individual pixels, small pixel clusters, etc.) are removed from the image. In accordance with the present invention, the purpose of this procedure is to eliminate small objects having a diameter that is too small for the laser cutting process, before the cutting operation. In this context, the value below which an object is considered to be too small for the laser cutting process, is settable. In this connection, the morphology known from the image analysis processes may be used. Image analysis morphology is discussed in detail in Sierra, J., "Image Analysis and Mathematical Morphology", Academic Press, 1988. In the described method, erosion is employed in particular as a special morphological filter for image processing. By selecting the magnitude of the morphological operator (SE=structuring element, term from mathematical morphology) or, however, in equivalent manner, by selecting the number of cycles in which an SE of a specific size is applied to the binary image, the user may set the particle sizes that are to be excluded before the laser cutting. Moreover, by utilizing the possibilities offered by image analysis morphology, it is also possible for very specific shapes, thus not only object sizes, but also objects having specific shapes, to be filtered out from the image. Thus, for example, lanceolated small objects may be successfully ignored, while small round objects are delivered to the cutting process, unfiltered.

Step 106: Segmentation and Determination of the Object Features:
In this analysis step, the object features of each segmented object are first determined (so-called feature extraction). The features utilized for the object classification are determined from the binary image and subsequently termed classification features. Classifiable features include all features which are presently measurable by image analysis or which are derivable from a priori knowledge, as well as any given linear combination of the parameters. Examples of features are surface area, convex surface, equivalent diameter, length, width, angle, orientation, roundness, length-width ratio, bulging, color values in RGB metric or any other color metric, curve length, curve width, horizontal and vertical projection, texture, energy, etc.

A very important feature is the position of the so-called FCP or feature count point (a well defined start point for describing the position of an object). By FCP, one understands one particular, distinct boundary pixel in the binary image, for example the lowermost, furthest right pixel in the binary object or, however, the topmost, furthest left pixel. Effectively, therefore, it is used as a start point for the contour around each binary object.

Once the objects in the binary image are measured, a list is created including the features of all of the objects.

TABLE 1.2

(Example) Features Measured For All Binary Image Objects

| | FCP x | FCP y | Surface area ($\mu m^2$) | Length ($\mu m$) | Roundness | ... Other |
|---|---|---|---|---|---|---|
| object 1 | 10 | 23 | 10 | 23 | 1.2 | ... |
| object 2 | 26 | 123 | 100 | 433 | 1.4 | ... |
| object 3 | 234 | 28 | 4711 | 345 | 2.5 | ... |
| object 4 | 165 | 278 | 2364 | 9721 | 1.8 | ... |
| ... | | | | | | ... |
| object n | 276 | 345 | 1254 | 3453 | 2.3 | ... |

Step 107: Object Classification:
In the next step, the extracted object features are compared to the predefined classification features. To that end, the combinations of measured object features of the objects to be cut out using the laser are checked for conformity with the values of the classification features. In this manner, the desired objects to be cut out are differentiated from those that are not desired. Since a number of characterizing features were specified for the desired objects of the same type, and since other features were specified for objects of another type, all objects may be uniquely assigned to one such type or be classified as waste, thus as unusable material. The unusable objects are then separated out and, thus, also not cut out.

An example in this regard is given in the following:

TABLE 1.3

(Example) Object Identification by Feature Regions

| | Measured surface area ($\mu m^2$) | Comparison value of the surface area ($\mu m^2$) | Assessment whether the object should be cut out |
|---|---|---|---|
| object 1 | 10 | 5 ... 500 | 10 within interval [5, 500] = cut out |
| object 2 | 100 | 5 ... 500 | 100 within interval [5, 500] = cut out |
| object 3 | 4711 | 5 ... 500 | 4711 outside of interval [5, 500] = DO NOT cut out |
| object 4 | 2364 | 5 ... 500 | 2364 outside of interval [5, 500] = DO NOT cut out |
| ... | | | ... |

TABLE 1.3-continued (Example) Object Identification by Feature Regions

| | Measured surface area (µm²) | Comparison value of the surface area (µm²) | Assessment whether the object should be cut out |
|---|---|---|---|
| object n | 1254 | 5 . . . 500 | 1254 outside of interval [5, 500] = DO NOT cut out |

In Table 1.3, each measured object surface is compared to a range of surface area values. In the example, an object is identified when its measured surface area lies within the predefined comparison values or limiting values. If the comparison is true, thus if the measured surface area (for example, 10 µm²) is within the range of values [5 µm², 500 µm²], then the object is accepted and ultimately cut out by the laser. This may be formally expressed as:

when $S_{measured} \in$ rangeofvalues $\Rightarrow$ then cut out particles;

when $S_{measured} \notin$ rangeofvalues $\Rightarrow$ then do not cut out particles, S denoting the surface area of the object. The user may, of course, also define other criteria for the cutting out process.

Thus, of course, objects that are not within the range of values, may be cut out by laser:

when $S_{measured} \notin$ rangeofvalues $\Rightarrow$ then cut out particles;

when $S_{measured} \in$ rangeofvalues $\Rightarrow$ then do not cut out particles.

By introducing the following notation, $SR = S$ is within the range of values; $\overline{SR} = S$ is not within the range of values, it becomes clear that any combination of measured features, each provided with an individual range of values, may be used to define a criterion for identifying specific objects to be cut out from the specimen.

TABLE 1.4

(Example) Various Features within the Previously Defined Range of Values

| | |
|---|---|
| SR | surface area within the range of values |
| RR | roundness within the range of values |
| LR | length within the range of values |
| CR | color within the range of values |
| . . . | . . . other features within the range of values . . . |

Thus, one could define the condition for cutting out as cut out when $SR+RR=LR+CR$ or, however, as cut out when $SR+\overline{RR}+\overline{LR}+CR$.

The latter signifies that an object is cut out by the laser when the surface area of the measured object is within the range of values, the roundness and the length each lie outside of the range of values in question and, at the same time, the color of the object is within the range of values.

Since it is possible in this manner for a great number of individual measured features to be compared with their corresponding ranges of value and for many features to be combined, virtually every object in the image is uniquely identifiable by a specific set of features. In addition, different object types may be recognized and individually collected in different collection vessels. For example, two object types may be individually differentiated on the basis of object 1: cut out when $SR1+RR1$ and object 2: cut out when $SR2+SR2$ in the case that R1 does not equal R2. Since the system includes different collection vessels for the microdissected material, various objects may also be individually collected.

Step 108: Automatic Determination of the Cutting Lines for the Laser:

Once the objects designated for microdissection are identified, the cutting operation is prepared in the last step in accordance with FIG. 1.2. The object contour of each identified object is first determined through image analysis. This object contour is indicated on the specimen in the xy coordinates where the laser is to perform the cutting operation. In this manner, a cutting line is automatically determined by the system.

Prior to the automatic cutting line determination, however, the identified objects may still be selectively subjected to further process steps, as described in the following. For example, groups of objects situated closely together are clustered in the image, i.e., combined into one shared object group to be cut out, as shown in FIG. 1.3. Here, four objects 34 disposed in close proximity to one another form one cluster 35. A shared, externally surrounding outer cutting line 36 is then defined for this cluster. The laser is thus prevented in accordance with the present invention from "slicing through" adjacent specimen objects during the cutting operation, as these objects are too closely proximate to the object actively being cut out (compare FIG. 1.3). Here as well, the morphology may be employed: In the present exemplary embodiment, a clustering is achieved by morphological closing, in image analysis, n-times closing meaning the sequential execution of n dilations, followed by n erosions. This principle is known from Schnaider; see http://www.zgdv.de/zgdv/departments/z2/Z2Staff/schnaide/local images/ME200 3-02.pdf.

Moreover, as illustrated in FIG. 1.4, internal "holes" in clusters may be specially handled during the cutting operation for objects intended for microdissection. In this case, a hole 37 is, in fact, produced by the clustering of a plurality of objects 34. However, in the interior of this formed cluster 35, a certain region, thus hole 37, is empty, thus devoid of any objects designated for microdissection. An inner cutting line 38 and an outer cutting line 36 are defined. The order of the cuts is then such that first the hole is cut out along inner cutting line 36 and, only then, is actual cluster 35 cut out along outer cutting line 36. In this way, the "purity level" of cut-out regions is not diminished by the material of the interior "holes."

By comparing the object position to the image edge position, it may additionally be ascertained whether or not a classified object touches the edge of the video image. In this manner, incomplete objects that are "cut off" by the image edge are prevented in accordance with the present invention from being likewise incompletely cut out by the laser. Thus, the system may offer the following option to the user, for example as a software selection or by selector control:

If the object touches the image edge, then do not cut out the object!

Preferably, this option may be optionally switched on and off by the user.

Moreover, the method according to the present invention makes it possible for the ed objects to be assigned to different object types. To that end, different groups of classification features are predefined for the different types of objects in the specimen. When the object features of an object conform with a specific group of classification features, the object is classified and assigned in this manner to the object type defined by the classification features. In one special embodiment, the system has a visual learning mode which enables a user who does not have extensive knowledge of image analysis methods to define new or additional criteria for the cutting out process. To that end, the user merely uses the computer mouse to select the desired objects or object types on the monitor. The system then automatically determines the classification features for the selected objects or object types.

Determination of the Cutting Lines:

In one possible embodiment of the method, the laser is guided over the specimen by a deflection unit for the x, y directions and, in this manner, cuts regions out of the specimen. In another embodiment, the laser beam is held immovably, and the x-y stage is moved. A combination of stage motion and laser beam guidance is also possible. In order to obtain a defined cutting profile, the laser is guided in relation to the specimen along a curve. The curve is defined by a series of x, y coordinates.

Since the specimen or a section of the specimen is viewable on the monitor via the camera, and since a mapping instruction exists which maps the pixel coordinates of the image onto corresponding coordinates of the laser motion, curves drawn in the monitor display may be converted into a laser cutting line. To that end, the coordinates of the curve in the monitor image may be transferred to the laser motion by an affine transformation.

This means, a linear mapping is provided $$f_u: V \to V$$

for a vector $$u \in V$$

where $$u: V \to V.$$

Thus, every point on the image is mapped by linear mapping onto a point on the specimen that is able to be reached by the laser or by the laser deflection unit. It holds that:

$$\begin{pmatrix} x' \\ y' \end{pmatrix} = \begin{pmatrix} a_{11} & a_{12} \\ a_{21} & a_{22} \end{pmatrix} \cdot \begin{pmatrix} x \\ y \end{pmatrix} + \begin{pmatrix} x_T \\ y_T \end{pmatrix}$$

(x', y') being the laser position and (x, y) the image coordinate position and ($x_T$, $y_T$) a linear displacement vector.

This fact is utilized in accordance with the present invention in order for the previously identified and classified specimen objects to be automatically cut out.

To this end, in the first step, the object contour around each individual identified and classified specimen object is determined. To compute the object contour, the so-called Freeman or chain code may be used.

To clarify the procedure for ascertaining a contour line, in FIG. 1.5, one single binary object is drawn in. The pixels of the image detail in FIG. 1.5 are characterized in accordance with their x, y coordinates. The size of the test image in FIG. 1.5 is 11×8 pixels. The binary object is marked by gray colored squares which represent the image pixels. The outside contour of the gray squares (=pixels) marks the external object boundary. It is essential to determine this boundary, because it is used as a basis for later determining the laser cutting line. If the laser, mapped accordingly, were directed along the sequence of coordinates {{7,1}, {8,1}, {9,2}, ... {6,3}, {7,2}} of the gray pixels, then the object would be cut out.

The top-most, furthest left binary object point, point {7,1}, is selected as a cutting start point. This reference point is generally referred to in the following as feature count point (FCP). An FCP is always the start point and, as does every pixel, has an x-y coordinate. In the following, for each binary image object, the top-most, furthest left contour pixel belonging to each object is defined as the feature count point FCP. Of course, any contour pixel may be defined as an FCP; it is merely important that there be a unified definition.

In order to automatically determine the laser cutting line from an image, a binary image must first exist which contains the image objects of interest as a binary pattern. When such a binary image exists, then all of the image objects have the same grayscale value.

To define the contour line for the laser cutting operation, the binary objects in the binary image are first labeled, i.e., each object is assigned one single, constant grayscale value, which is assigned to all of its pixels, for instance grayscale value 3 for all pixels of an object, etc. From the binary image, a grayscale image is effectively regenerated, in which all pixels belonging to one cohesive object are assigned one uniform, unique grayscale value. FIG. 1.6 shows four objects 28, 29, 30 and 31, which are each represented by one contiguous pixel set. Each object, which previously had one uniform grayscale value in the binary image, is now labeled with one individual grayscale value.

In FIG. 1.6, for instance, object 29 is given grayscale value 2. Thus, this object was labeled with grayscale value 2.

In the next step, the outer pixels, thus those pixels located on the outer boundary of the object, are determined for all objects. To that end, all of the holes in one object are first closed. In this context, those pixels which are completely surrounded by pixels having a different grayscale value, are designated as the hole. Such an example is illustrated in FIG. 1.6 by object 31. In this example, this object 31 has an interior hole composed of two contiguous pixels. A determination as to whether an object has holes may be made based on the Euler number:

$$E = K - L$$

where $E$=the Euler number; $K$=the number of objects; $L$=the number of holes.

The Euler number is a topological feature and, therefore, does not change when simple transformations are made. If all holes are closed within the individual objects prior to the transformation, i.e., L=0 and E=K, then no more hole contours occur when the image is mapped onto the laser cutting line.

The outer contour of each image object, which does not have any more holes, may subsequently be easily defined. To this end, it must be ascertained that every pixel which is entirely situated within an object, is completely surrounded by object pixels of the same grayscale value. Therefore, any pixel that is not completely surrounded by object pixels, must belong to the outer boundary of the object, if the object does not have any holes. This criterion is checked for each pixel, and the boundary pixel is determined in this manner.

The boundary pixels for an object are encoded in accordance with the Freeman instruction and stored in the list of values assigned to the object. In this context, for the directional encoding, an eight-pixel neighborhood is used, i.e., each pixel is surrounded by eight other pixels. In principle, a four-pixel neighborhood may also be employed, in which either the four diagonally neighboring pixels or the four non-diagonally neighboring pixels are considered. An eight-pixel neighborhood yields a higher accuracy, while a four-pixel neighborhood is able to be computed more rapidly.

In FIG. 1.7a), such an eight-pixel neighborhood for a Freeman code is shown. The central pixel is surrounded by eight neighboring pixels. The Freeman notation now assigns a unique number to each neighboring pixel that represents a specific incremental direction. The object contour is subsequently traversed, starting from an FCP.

In FIG. 1.7b), the boundary pixels of an object are shown. In this example, the FCP is the furthest left, topmost pixel. This point is the starting point. Starting from this point, the next pixel position is determined in the clockwise direction, for example. In accordance with the Freeman code, as shown in FIG. 1.7a), the next pixel is found at position 3. From this pixel, the next pixel is considered at position 3; from this pixel, the next pixel is considered at position 5; etc.

Since each object contour is completely measured off in steps, or incrementally scanned, starting from the particular FCP, a Freeman code in the form of a number chain is obtained, which fully describes the contour of the particular object. Since, in addition, the coordinates of the FCP are stored for each object, all of the objects in the image are fully describable in terms of contour and position. FIG. 1.7c) shows the corresponding notation of the Freeman code for the boundary pixels of the object shown in FIG. 1.7b). Using this encoding method, a list encompassing the contour data on all of the objects is generated as an interim result. It includes the particular position of the FCP, starting at which an object contour must be described.

TABLE 1.5

(Example) Determining the Laser Cutting Code by Applying a Contour Analysis Method

|  | FCPx | FCPy | Freeman code describes the outer laser cutting line of the object |
|---|---|---|---|
| object 1 | $x_1$ | $y_1$ | 2333563345673000 . . . |
| object 2 | $x_2$ | $y_2$ | 42233467776002345 . . . |
| object 3 | $x_3$ | $y_3$ | 6673332221176600333 . . . |
| object 4 | $x_4$ | $y_4$ | 336522100655 . . . |
| . . . |  |  |  |
| object n | $x_n$ | $y_n$ | 223566676553211000 . . . |

From the Freeman code and the FCP coordinates, the exact x-y position of any one pixel is computed. In this way, the laser cutting line is initially completely described. In principle, however, other encoding methods are also possible.

If a Freeman encoding is employed as shown in FIG. 1.7, then the following conversion table is derived for the next respective pixel position in x, y:

TABLE 1.6

(Example) Conversion of the Freeman Code into Actual Pixel Coordinates

| Freeman code | Last pixel position | dx | dy |
|---|---|---|---|
| 0 | $x_{last}, y_{last}$ | −1 | −1 |
| 1 | $x_{last}, y_{last}$ | 0 | −1 |
| 2 | $x_{last}, y_{last}$ | +1 | −1 |
| 3 | $x_{last}, y_{last}$ | +1 | 0 |

TABLE 1.6-continued (Example) Conversion of the Freeman Code into Actual Pixel Coordinates

| Freeman code | Last pixel position | dx | dy |
|---|---|---|---|
| 4 | $x_{last}, y_{last}$ | +1 | +1 |
| 5 | $x_{last}, y_{last}$ | 0 | +1 |
| 6 | $x_{last}, y_{last}$ | −1 | +1 |
| 7 | $x_{last}, y_{last}$ | −1 | 0 |

In this context, the starting values of the FCP are used at the beginning:

$$x_{last} = x_{FCP}$$

$$y_{last} = y_{FCP}$$

The Freeman code is subsequently followed along the contour. At the end of this procedure, the laser cutting code is known for each identified and classified image object, which, by applying the transformation $$\begin{pmatrix} x' \\ y' \end{pmatrix} = \begin{pmatrix} a_{11} & a_{12} \\ a_{21} & a_{22} \end{pmatrix} \cdot \begin{pmatrix} x \\ y \end{pmatrix} + \begin{pmatrix} x_T \\ y_T \end{pmatrix},$$

is transferred from the image coordinates to the corresponding laser coordinates. Translation vector $\{x_T, y_T\}$ may shift the laser cutting line.

Moreover, the ascertained laser cutting line surrounding the object is scaled as a function of the type of imaging being used. The intended purpose here is to evaluate, by image analysis, objects which are at a lower resolution (lower magnifying objective) and subsequently, after manually or automatically switching the microscope to a higher resolution (=higher magnifying objective), to cut out the classified objects by laser beam. Since the laser cutting line is known as a vector representation, the laser cutting lines ascertained at low magnification are scaled, virtually losslessly, to the higher resolution image.

Since switching to a higher magnification is associated with a scaled down image field, many of the cutting lines lie outside of the actual image field and, therefore, at first, can no longer be reached by the laser beam. However, since the laser cutting line positions outside of the active field of view are known, they may be repositioned by automatically adjusting the microscope stage position. This is accomplished by employing suitable means, such as an automatic stage, an automatic objective change, etc.

When working with very high magnifications and small objects, the stage positioning accuracy is improved, if required, by the additional use of piezotranslators for the x and y directions of the stage. In this context, substantially the same result may be achieved by using piezotranslators to adjust the specimen holder. Since the laser beam is deflected in the incident light axis by a deflection unit and cuts in the process and, moreover, since the objects to be cut out have previously been automatically determined with respect to their position, a highly precise and rapid microdissection of the automatically ascertained objects is accomplished by the deflection unit, by combining the stage motion to move to the optimal cutting position (in the vicinity of the optical axis) and the laser cutting along the automatically ascertained laser cutting line.

In addition, by beneficially combining the simultaneous motion of the laser beam in response to the deflection unit in the incident light axis and the "normal" microscope stage motion, as well as the finer resolution produced by the additional use of piezotranslators, the automatically ascertained laser cutting lines may be approached more rapidly. In this context, the actual cutting process is carried out by the deflection unit in the incident light axis, while the coarse and fine positioning of the objects is achieved by suitable automatic motions of the actuators involved (=piezotranslators) for the x-y positioning.

The problem which arises from the necessity of having to refocus after switching over to a different resolution mode, i.e., to another objective, is resolved by the use of an autofocusing device. The requisite speed is achieved by the use of a piezo-focusing device on the objective, i.e., the objective is moved vertically by the piezotranslator.

Other possible focusing approaches include manual focusing, or also the use of stepper motors for an electronically controlled focusing via the vertical z-axis of the microscope. The advantage of rapid automatic focusing derived in accordance with the present invention is that an optimal laser cutting process may be executed when the laser is always focused in the desired cutting plane, i.e., the specimen plane.

In fully automatic processes, such as automatic laser cutting line determination followed by the subsequent process of cutting out a large number of objects, an automatic and rapid focusing is absolutely essential.

Allowing for the Width of the Laser Cut:

Since a laser beam cut has a certain width that must be considered, cutting directly at the outer edge of an object results in parts of the object edge burning as well. This results in unwanted artifacts in the subsequent analysis. These biological artifacts are produced because the burning of the boundary structure leads to a change in the molecular structure in the boundary regions of the objects. Since in most cases, however, the objects are cut out and collected in order to determine their properties in subsequent biochemical analysis steps (for example using PCR), it is essential to prevent burning in the boundary regions of an object. This is accomplished by directing the cutting laser beam at a certain settable clearance distance around the object in such a way that no burning artifacts can occur.

Exemplary Embodiment 1

One exemplary embodiment is the application of mathematical morphology to the binary image which is formed as an intermediate processing step in the process of determining the laser cutting line. Since the binary image is formed before the laser cutting line profile is determined, thus before the cutting line is computed using the Freeman code and converted to x-y coordinates (as described further above), a manipulation of the binary image influences the contour determination.

The binary objects are enlarged by dilation of the binary image (dilation=morphological image processing step). To accomplish a preferably most symmetrical possible enlargement, a symmetrical element, which dilates true-to-scale and independently of direction, is selected as a structuring element SE. This may be a so-called disk element (see Sierra, for example). To distort the object, a different SE may also be selected, which meets the necessary morphological requirements. Moreover, the dilation may be applied to the image objects in repeated cycles, each image object in the binary image being enlarged each time by a specific pixel amount.

When an appropriate SE is selected, the object expands by only about one pixel in each direction in each application cycle. This means that the object diameter expands by approximately two pixels in each application (cycle) of one single dilation step using this SE.

In addition, by calibrating the image pixels, the size of one pixel may be ascertained in μm. Therefore, in the case of the square pixels typically used $dx_{pixel}=dy_{pixel}$=size of a pixel following calibration.

Since the laser beam has a known cutting width, it is possible to determine the requisite object enlargement, i.e., the number of dilation steps required to direct the laser beam at a safe clearance distance around the object.

Example laser beam–cutting cross section $L_s$=8 μm pixel size (calibrated) $P_k$=1 μm object enlargement per dilation $D_{z=1}$=2 pixels
(z=number of cycles)

required clearance distance of the laser from the object $L_{clearance\ distance}=L_s/2$=4 μm number of cycles required for dilations $Z_D$ in order to reach desired laser clearance distance $Z_D=L_{clearancedistance}/P_k$=4 dilation cycles.

This means that, after four dilation cycles, a virtual object size is obtained, whose outer contour the laser would be directed around at the correct clearance distance from the actual object (prior to the artificial expansion). Since the laser cutting lines are computed on the basis of the virtual objects which have been appropriately enlarged by dilation (as described above), the laser beam is directed at the desired clearance distance from the object boundary, and it cuts out the object safely and without burning the object boundary regions.

Exemplary Embodiment 2

In another exemplary embodiment, the vectorization of the cutting line that had previously been computed in accordance with the above known method for automatically determining laser cutting lines, is taken as a basis.

Every point of the laser cutting line undergoes a scaling transformation. This is accomplished by enlarging the laser cutting line to the extent desired and by directing the laser beam around the object at a safe clearance distance to ensure that the object is cut out without being damaged.

In the following, it is assumed that the laser cutting line is already known by having been previously defined (automatically or manually). The laser cutting line is composed of a series of points $P_i$ having coordinates $(x_i, y_i)$ and is completely described by the same. In the case of scaling, it holds for every point P that $x'_i=sx \cdot x_i$ $y'_i=sy \cdot y_i$ sx and sy being scaling factors. In vector notation, this is described as $$P_i = \begin{pmatrix} x_i \\ y_i \end{pmatrix} \quad S = \begin{pmatrix} sx & 0 \\ 0 & sy \end{pmatrix} \quad P'_i = \begin{pmatrix} x'_i \\ y'_i \end{pmatrix},$$

$P_i$ being the i-th original point and $P'_i$ the i-th scaled point of the laser cutting line. Thus, the scaling equation is expressed as $$P'_i = S \cdot P_i$$

for all points i from the interval [0, k] of the laser cutting line. In this procedure, the laser cutting line is scaled in such a way that the object is able to be cut out at a safe clearance distance. The distances, by which the individual contour points are spaced apart and which are a consequence of this type of scaling, are compensated in that the laser beam cuts in straight lines from point $P_i$ to point $P_{i+1}$. Thus, given substantial enlargements, the continuously extending laser cutting line approximates a polygon in that individual points Pi are joined by straight segments of the laser cutting line.

In addition, imaging distortions (aberrations) may be compensated by a suitable, location-dependent adaptation of the scaling matrix, thus:

$$P'_i = S_i \cdot P_i$$

Transformation of the Laser Cutting Lines

To adapt the cutting lines to different circumstances, one utilizes the fact that the automatically computed laser cutting line exists as a series of points $P_i = P(x_i, y_i)$. By transforming these points into a new series of points, any desired distortion, displacement or rotation of the laser cutting line is able to be achieved in order to compensate for laser cutting errors. Thus, for example, aberrations of the lens system imaging the laser beam could be compensated.

In the following, various compensation methods are described exemplarily.

Error Compensation or Manipulation by Translation

The cutting line is shifted by dx and dy. The values for dx, dy are derived from the errors ascertained in each instance, or from the desired laser cutting line manipulations $$x'_i = x_i + dx$$
$$y'_i = y_i + dy$$
$$P_i = \begin{pmatrix} x_i \\ y_i \end{pmatrix} \quad T = \begin{pmatrix} dx \\ dy \end{pmatrix} \quad P'_i = \begin{pmatrix} x'_i \\ y'_i \end{pmatrix}$$

or in contracted notation $$P'_i = P_i + T$$

Distortions may be compensated by adaptive translation, specifically by a location dependency of the translation value $$P'_i = P_i + T_i$$

This measure makes it possible, for example, to selectively compensate for small deviations in the precision of the microscope stage repositioning.

Error Compensation or Manipulation by Scaling

The cutting line is scaled by sx and sy. The values for sx, sy are derived from the errors ascertained in each instance, or from the desired laser cutting line manipulations $$x'_i = sx \cdot x_i$$
$$y'_i = sy \cdot y_i$$
$$P_i = \begin{pmatrix} x_i \\ y_i \end{pmatrix} \quad S = \begin{pmatrix} sx & 0 \\ 0 & sy \end{pmatrix} \quad P'_i = \begin{pmatrix} x'_i \\ y'_i \end{pmatrix}$$

or in contracted notation $$P'_i = S \cdot P_i$$

Distortions may be compensated by adaptive translation, specifically by a location dependency of the scaling value:

$$P'_i = S_i \cdot P_i$$

By implementing this measure, distortions caused by lens errors, for example, are compensated. The following possibilities for influencing the laser cutting lines are derived

TABLE 1.7

| | Possibilities for Scaling the Laser Cutting Line in the x Direction (in Terms of y) | |
|---|---|---|
| $P_i(x_i)$ | Scaling value sx | $P'_i(x'_i)$ |
| if $x_i > 0$ | sx = 0 | $x'_i$ is on the y axis |
| | sx = 1 | identical imaging |
| | sx = −1 | reflected into y axis |
| | sx > 1 | expansion |
| | sx < −1 | expansion and reflected |
| | sx < 1 AND \|sx\| > 0 | compression |
| | sx < 1 AND \|sx\| < 0 | compression and reflected |
| if $x_i < 0$ | sx = 0 | $x'_i$ is on the y axis |
| | sx = 1 | identical imaging |
| | sx = −1 | reflected into y axis |
| | sx > 1 | expansion |
| | sx < −1 | expansion and reflected |
| | sx < 1 AND \|sx\| > 0 | expansion |
| | sx < 1 AND \|sx\| < 0 | expansion and reflected |

Error Compensation or Manipulation by Rotation

The cutting line is rotated by an angle θ. The value for θ is derived from the laser cutting line manipulations desired in each instance $$x'_i = x_i \cdot \cos(\theta) - y_i \cdot \sin(\theta)$$
$$y'_i = x_i \cdot \sin(\theta) + y_i \cdot \cos(\theta)$$
$$P_i = \begin{pmatrix} x_i \\ y_i \end{pmatrix} \quad R = \begin{pmatrix} \cos(\theta) & -\sin(\theta) \\ \sin(\theta) & \cos(\theta) \end{pmatrix} \quad P'_i = \begin{pmatrix} x'_i \\ y'_i \end{pmatrix}$$

or in contracted notation $P'_i = R \cdot P_i$.

Distortions may be compensated by adaptive rotation of individual laser cutting line points, specifically by a location dependency of the angle of rotation $$P'_i = R_i \cdot P_i$$

By implementing this measure, rotational errors are compensated, for example.

Manipulation of the Laser Cutting Line by the Composition of Transformations

The manipulations mentioned above for adapting the computed laser cutting line to the particular circumstances or, however, for the purpose of correcting errors or, however, for other adaptation purposes may also be accomplished by the composition of various transformations. The benefit resides in the increased speed at which complex laser cutting lines are able to be computed and manipulated.

One advantageous embodiment of a laser microdissection device suited for implementing the method includes an appropriate user interface which allows the user to easily manipulate complex mappings of laser cutting patterns in a process that is transparent to the user.

To that end, the transformations must be converted to the 3×3 matrix notation. It holds for the transformations translation:

$$P_i = \begin{pmatrix} x_i \\ y_i \\ 1 \end{pmatrix} \quad T = \begin{pmatrix} 1 & 0 & dx \\ 0 & 1 & dy \\ 0 & 0 & 1 \end{pmatrix} \quad P_i' = \begin{pmatrix} x_i' \\ y_i' \\ 1 \end{pmatrix}$$

scaling:

$$P_i = \begin{pmatrix} x_i \\ y_i \\ 1 \end{pmatrix} \quad S = \begin{pmatrix} sx & 0 & 0 \\ 0 & sy & 0 \\ 0 & 0 & 1 \end{pmatrix} \quad P_i' = \begin{pmatrix} x_i' \\ y_i' \\ 1 \end{pmatrix}$$

rotation:

$$P_i = \begin{pmatrix} x_i \\ y_i \\ 1 \end{pmatrix} \quad R = \begin{pmatrix} \cos\theta & -\sin\theta & 0 \\ \sin\theta & \cos\theta & 0 \\ 0 & 0 & 1 \end{pmatrix} \quad P_i' = \begin{pmatrix} x_i' \\ y_i' \\ 1 \end{pmatrix}$$

composition examples:

$P_i' = T_1 \cdot T_2 \cdot P_i$ (two translations are performed)

$P_i' = S_1 \cdot S_2 \cdot P_i$ (two scalings are performed)

$P_i' = R_1 \cdot R_2 \cdot P_i$ (two rotations are performed)

$P_i' = S_1 \cdot T_1 \cdot R_1 \cdot P_i$ (rotation, translation, and scaling are performed).

By combining the transformations, the laser cutting line previously automatically ascertained or already known by other means, when it is only known as a series of points where $P_i = P(x_i, y_i)$, may be rotated, scaled, and displaced in any manner desired. In particular, the same cutting patterns are repeatable, permitting an array of substantially identical cutting patterns to be cut out.

It is also possible to combine the individual transformations per matrix multiplication (the sequence of the combinations generally not being commutative).

Thus, because the laser cutting line is represented as a series of points, all known operations from linear algebra may be employed to represent the laser cutting in the simplest possible manner and in a manner that is highly understandable and transparent to the user.

FIG. 2 shows a laser microdissection device for implementing the method according to the present invention which, in this exemplary embodiment, moves a laser beam over a sample that is held in position during the cutting operation. In another embodiment (not shown), the laser beam is held immovably, and the specimen is moved relative thereto.

The laser microdissection device encompasses a microscope 1 having a movable x-y stage 2, on which a specimen holder 3 is mounted. In this embodiment, an upright microscope is used. For this purpose, however, a set-up including an inverted microscope is also possible.

A specimen 4, from which an object is to be cut out, is positioned on the bottom side of specimen holder 3. An illumination system 5 and a condenser lens 11 for illuminating specimen 4 are located underneath x-y stage 2. In this specific embodiment, x-y stage 2 is not moved horizontally, i.e., in the x- or y-direction, during the cutting operation. Disposed underneath specimen 4 is at least one collection vessel 19 for collecting the microdissected piece.

A laser beam 7 is emitted by a laser 6, in this example a UV laser, and is coupled into an illumination beam path 20. A laser scanning device 22 is mounted in the illumination beam path 20. Laser beam 7 passes through laser scanning device 22 and arrives via an optical system 13 at an objective 9 which focuses laser beam 7 onto specimen 4. Optical system 13 is advantageously designed as a dichromatic beamsplitter through which an imaging beam path 21 originating at specimen 4 passes through objective 9 to arrive at least one eyepiece 12.

In this embodiment, the adjustment of laser scanning device 22 and thus positioning of laser beam 7 on specimen 4 are accomplished by a motor 23 assigned to laser scanning device 22, a control unit 24, and by a computer 16. Motor 23 is linked to control unit 24 which delivers the control signals for driving motor 23. Control unit 24 is linked to computer 16 which has a monitor 18 connected thereto. An image detail of specimen 4 captured by a camera 17 is displayed on monitor 18. A desired nominal cutting line may be defined in the camera image on monitor 18 using a computer mouse (not shown) or any other cursor control device. Moreover, computer 16 is connected to laser light source 6 to which it only delivers trigger signals for triggering laser pulses when a cutting operation is performed.

Laser scanning device 22 itself is used as a cutting-line control unit which generates a relative motion between laser beam 7 and specimen 4 during the cutting operation. A user may focus laser beam 7 by manually adjusting the height of x-y stage 2 while simultaneously visually monitoring the camera image. However, an embodiment of the device which includes an autofocusing device (not shown) for laser beam 7 is more user-friendly.

In response to control of laser scanning device 22, laser beam 7 emerges at the output thereof at various deflection angles. In the process, by varying the deflection angle, laser beam 7 may be directed to any given positions on specimen 4 which are located within the field of view of objective 10.

Image analysis software, which is used for processing the image captured by camera 17 and for automatically ascertaining, in the image, at least one object to be cut out in accordance with the method of the present invention, is installed on computer 16. A nominal cutting line surrounding the object is subsequently automatically determined for the object.

The cutting width of a laser in a sample is dependent on the laser parameters, such as laser power and aperture of laser beam 7. Depending on the currently set cutting width, a number of nominal positions of the laser beam on sample 4 are computed for the nominal cutting line that is automatically defined in accordance with the method, the sequentially disposed nominal positions of laser beam 7 yielding the desired nominal cutting line.

With the aid of laser scanning device 22, the nominal positions are then approached one after another on sample 4. Each time that laser scanning device 22 prepares or sets the nominal position of laser beam 7 on sample 4, computer 16 delivers trigger signals for triggering laser pulses to laser light source 6. In this manner, the laser cut is incrementally generated in the specimen.

Once the laser cutting process is complete, the microdissected piece is completely separated from the surrounding specimen 4 and, in this arrangement, falls under the force of gravity into collecting vessel 19 subjacent thereto.

Special Embodiments of the Method

In the following, various special embodiments of the method are also indicated.

Another embodiment of the method is characterized in that an automatic shading correction is additionally provided, encompassing the following steps:
- manual or automatic positioning of the microscope stage at a position that is either preprogrammed as a DEFAULT position or, alternatively, had previously been programmed in, which makes it possible for an empty image, thus an image of inhomogeneous illumination, to be recorded;
- storing of this shading correction image as a reversible image data format (TIF=tagged image file (image format), BMP=bitmap (image format), etc.);
- and use of the stored shading image for subsequent images, in which objects are to be recognized, the intention being for these objects to be cut out by laser beam in order to eliminate the image distortion caused by the inhomogeneous illumination.

Another embodiment of the method provides additionally for automatic and manual detection of objects to be cut out. To that end, a suitable method is employed to place a preferably most favorable possible threshold value in the histogram, to produce an optimal binary image containing the maximum information possible on the objects to be cut out by laser. For example, an entropy maximization method may be applied to determine the optimal threshold value for automatically generating a binary image. Alternatively, the threshold value for generating the binary image may also be manually set.

The threshold values may be stored on data carriers and reactivated, permitting a repeated binarization of the object for the laser cutting method.

Another embodiment of the method provides for relatively small objects, which are not designated to be cut out by the laser, to additionally be eliminated. To that end, the following steps may be provided:
- relatively small objects are removed from the binary image using image analysis morphology, in particular erosion;
- a measure for the size of those objects, which are to be excluded from the laser cutting process, is set as a function of the number of erosion cycles;
- using geometrical factors, thus by utilizing the morphology of the image analysis operators employed, specific object shapes are excluded from the laser cutting process in that these objects are filtered out of the binary image.

Another embodiment of the method has the distinguishing feature of additionally preventing objects which are too closely proximate to one another in the specimen from being sliced through. To that end, image objects which are designated to be cut out by laser, but which are too closely proximate to one another, are combined into a cluster. This is accomplished by directing the laser cut around the outside of all the particles, thereby cutting out the entire, cohesive region of objects of interest. Consequently, no object of interest is "sliced through." In the process, mathematical morphology is used to determine the outside contour line for the laser cut.

In another embodiment of the method, objects or regions, the so-called holes, contained in the desired clusters, are separated from the clusters. To that end, the following steps are provided:
- a plurality of cutting lines, in particular two cutting lines, are computed in such a way that n cutting lines surround the hole or the holes and m cutting lines surround the object or the objects of interest;
- a specific cutting sequence is used to separate the holes from the objects of interest, thus from the clusters.

In microdissection systems which are based on an inverted microscope, in which the cut-out object or cluster remains on the specimen holder or on a slide, for example on a specimen slide or Petri dish, following the laser cutting operation, it is still possible for the holes contained in the cluster to be cut out after the actual cluster is cut out. However, if the cutting operation is performed in a microdissection system which is based on an upright microscope, the interior holes are cut out first and the actual clusters subsequently thereto.

It proves to be especially advantageous for the holes to be collected in different collection vessels than those used for the objects which are actually of interest. In this manner, the holes are disposed of appropriately as "waste material", and the purity level of the samples is increased. In the same way, the holes themselves may also be objects or regions that one is interested in for further analyses, so that they are collected separately.

Another embodiment of the method has the distinguishing feature of additionally providing for different objects in the specimen to be automatically detected and cut out on the basis of a feature extraction. In this context, the following steps are possible:
- the features of a group of objects are measured in an image to permit a laser micro dissection;
- the features of the measured objects are compared to predefined ranges of values which are individually specified for each feature.

For routine operations in the laboratory, it proves to be advantageous when the ranges of values used for recognizing and classifying the objects are able to be stored and loaded and, thus, exchanged in any given manner. In this connection, all electronic data carriers, networks, the Internet, written documents, spoken commands are considered to be storage media. The ranges of values used for recognizing and classifying the objects may be stored and loaded in databases. In addition, the ranges of values used for recognizing and classifying the objects may be altered and adapted by making external manipulations in databases or by using external programs.

In one especially advantageous embodiment, the ranges of values used for recognizing and classifying the objects may also be used for synchronizing a plurality of automatic laser cutting systems, which automatically determine laser cutting lines and which are connected via a data network to form a system cluster. This is accomplished in that all automatic laser cutting systems work under the same conditions. The system cluster may be formed via a local network, LAN, WLAN, Bluetooth, the Internet, or an intranet, etc.

In addition, any desired comparison formalism may be applied, the goal being to obtain a unique identification of a specimen object by combining the individual comparisons of the measured-object feature data with the individually predefined ranges of values. In the process, different objects may be recognized on the basis of individual feature data records. It is also advantageous that, in one sequence of operation, different objects may be cut out of the specimen and collected in collection vessels that have been individually and automatically prepared for the microdissected material.

In another advantageous embodiment of the method, image analysis is used to identify objects which "touch" the image edge, and such objects are subsequently not cut out by the laser. In this way, an incomplete object or an incomplete cluster is prevented from being cut out. Rather, only objects located entirely within the image are cut out by the laser.

By additionally employing contrasting methods based on microscope and/or camera technology, a specimen detail is presented by an imaging method, for example using a camera, so effectively that the laser cutting line may be automatically defined on the basis of this image, through image analysis.

In addition, by superimposing the automatically ascertained cutting lines using an imaging device, the results are able to be controlled. The results are displayed directly in the camera image of the laser cutting system or as a reflection into the visual microscope image.

When classifying the object features, the object contours are described by encoding their geometric contours. This is accomplished in such a way that the contour description, which is implemented automatically or semi-automatically from an image analysis, may be mapped directly onto the nominal cutting line and thus onto the laser cutting coordinates.

In another embodiment of the method, a learning process is provided for the object classification, that is able to automatically or manually determine the ranges of values required for classifying the objects that are to be cut out by laser. This learning process is conceived in such a way that the ranges of values are input using software or are automatically entered by suitably marking the objects, for example by a mouse click in the image of the specimen.

Objects which touch the image edge are not able to be completely cut out by laser. Moreover, due to the incomplete form, there is the danger of erroneous classification. Therefore, such objects are ignored when necessary, by checking during the object identification process to determine whether an object is touching the image edge or not. Then, in dependence upon the analysis result, the object may be blocked out prior to the further process steps.

An independence from the laser wavelength is achieved by automatically classifying and computing the laser cutting line by using laser wavelength-independent, imaging methods. To this end, for example, a microscope image having broadband illumination, for example in the visible spectral region, is recorded and processed.

By properly scaling the laser cutting line, the object classification and the determination of the laser cutting line may be undertaken at low magnification. The result is that a relatively large field of view is available, thereby permitting detection of more objects. Consequently, the actual microdissection process may be undertaken at a higher magnification.

The accuracy of the laser cut is enhanced through the use of piezoelectric actuators for the x-y displacement of the specimen. It also proves to be advantageous when x-y positioning devices are used to position the object and its laser cutting line in the vicinity of the optical axis, in order to obtain optimal cutting conditions. In this context, the deflection unit executes the microdissection process in the incident light axis of the microscope, while the stage automatically positions the objects to be cut out near the optical axis. By applying a proper linear combination of the motions of the microscope stage, the x-y piezotranslator, and of the deflection unit for the laser cutting operation, the cutting speed is increased, while the cutting precision is simultaneously enhanced.

Through the use of an autofocusing device, the cutting laser beam is always moved to the optimal cutting position, so that an automated process for cutting out any given number of objects is rendered possible without any monitoring by a user. The speed of the system is also substantially increased by the use of an autofocusing device in conjunction with a z-piezotranslator and/or a z-galvanometer positioning element. In this context, the objective is adjusted directly in the z direction by the z-piezotranslator and/or the z-galvanometer positioning element. In this manner, an automated process for cutting out any given number of objects may be performed without requiring any monitoring by a user.

Another embodiment of the method additionally provides for automatically changing the clearance distance of the laser cutting line from the object to achieve a microdissection free of artifacts. To that end, the coordinates of the individual points of the nominal cutting line are processed in that the image objects are suitably processed using image analysis prior to the actual laser cutting line determination in such a way that the processed nominal cutting line extends at a greater clearance distance from the segmented object. To that end, the binary image of the segmented object is preferably dilated prior to the cutting line computation, so that the object is enlarged in a determinate manner by the desired number of pixels. The enlarged objects are then used as a basis for the laser cutting line computation as described at the outset.

The coordinates of the individual points of the laser cutting line are increased by applying an appropriate scaling transformation, so that, during the actual laser cutting process, the laser beam is directed at a safe clearance distance around the object. To that end, the user adjusts the laser clearance distance via a software interface, which permits the testing of system settings, in particular with respect to the process automation. The laser clearance distance is automatically computed and adjusted in order to permit fully automatic processes.

Another embodiment of the method additionally provides for compensating for aberrations (for example distortions) when imaging the laser onto the specimen. To that end, the scaling factor is formulated as a function of position. Alternatively or in addition thereto, every laser cutting line contour point is individually distorted in such a way that aberrations of the microscope system and of the camera lens system, thus of all imaging elements, are compensated. In this manner, the ascertained nominal cutting line is converted to a laser cutting line precisely and without aberrations.

Yet another embodiment of the method additionally provides for the laser cutting lines that had previously been read in automatically or manually from a data carrier to be manipulated, linearly combined, and compensated for errors. To that end, the following steps are possible:

To compensate for a lateral error in the laser cutting lines computed in accordance with the above method, a matrix transformation is applied in order to translate all laser cutting line points by a specific amount in the x and y directions. Moreover, a matrix transformation may be applied to the laser cutting lines computed in accordance with the above method in order to scale all laser cutting line points by a specific amount in the x and y directions. Alternatively or in addition thereto, a matrix transformation may be applied to the laser cutting lines computed in accordance with the above method in order to rotate all laser cutting line points by a specific amount in the x and y directions.

In one special embodiment, any given combination of matrix transformations is applied to the laser cutting lines computed in accordance with the above method in order to incrementally translate and/or scale and/or rotate all laser cutting line points by a specific amount in the x and y directions. By employing matrix transformations, in particular the translation matrix, any imprecise repositioning of the microscope stage is compensated (=return to microscope stage positions). To that end, the ascertained laser cutting line is corrected by a specific amount dx, dy, which corresponds to the amount by which the microscope stage repositioning is inaccurate. The compensation processes are carried out by directly manipulating the coordinate matrix of a laser cutting line pattern, thus without active stage movement, but are effected solely by the deflection unit of the laser in the incident light axis of the microscope.

By repeating any given number of laser cutting line patterns, an array of laser cutting lines is generated per cyclically repeated matrix transformation in any desired patterns. This renders possible a statistical sampling of large, substantially identically shaped samples from a specimen.

The manipulation factors, linear combinations and error compensation factors may be suitably stored on electronic data carriers or in databases, etc., and reactivated. Thus, a user-specific device profile may be stored and reactivated as needed.

LIST OF REFERENCE NUMERALS 1. microscope
2. movable x-y stage
3. specimen holder
4. specimen
5. illumination system
6. laser
7. laser beam
8. microscope stand
9. objective lens
10. optical axis
11. condenser
12. eyepiece
13. optical system
14. aperture
16. computer
17. camera
18. monitor
19. collecting vessel
20. illumination beam path
21. imaging beam path
22. laser scanning device
23. motor for the laser scanning device
24. control unit
25. object 1
26. object 2
27. object 3
28. object 1 having grayscale value 1
29. object 2 having grayscale value 2
30. object 3 having grayscale value 3
31. object 4 having grayscale value 4
32. neighboring pixel
33. central pixel
34. object(s)
35. cluster
36. outer cutting line
37. hole
38. inner cutting line

What is claimed is:

1. A method for laser microdissection comprising:
   capturing an electronic image of at least one image detail of a specimen;
   processing the at least one image detail using image analysis so as to automatically ascertain at least one object to be cut out;
   automatically calculating a contour of the at least one object;
   automatically defining, based on the calculated contour, a nominal cutting line around the at least one object to be cut out; and
   subsequently cutting out the at least one object in response to a relative motion between a laser beam and the specimen.

2. The method as recited in claim 1 further comprising preparing the electronic image for the processing using a contrasting method based on camera or microscope technology.

3. The method as recited in claim 1 wherein the processing the image detail is performed using a segmenting of the electronic image:
   defining a grayscale threshold value on the basis of the electronic image; and
   converting, by making a comparison with the grayscale value threshold, the electronic image to a binary image including only the at least one object segmented.

4. The method as recited in claim 3 wherein the defining a grayscale threshold value is performed by manually setting the threshold value or automatically defining the threshold value in an entropy maximization process.

5. The method as recited in claim 3 wherein the processing the image detail includes:
   defining specific classification features characterizing the at least one object so as to ascertain the at least one object;
   classifying the at least one object using image analysis by determining from the image actually existing object features of the at least one object segmented and comparing the existing object features to the defined specific classification features.

6. The method as recited in claim 5 wherein the comparing is performed so as to determine whether the actually existing object features conform with the defined specific classification features.

7. The method as recited in claim 5 wherein the defining specific classification features includes defining, in each instance for different object types, individual feature data records including the specific classification features.

8. The method as recited in claim 5 wherein the defining specific classification features is performed automatically or manually in a learning process including inputting the classification features interactively or automatically by suitably marking the at least one object.

9. The method as recited in claim 8 wherein the marking is preformed using a mouse click.

10. The method as recited in claim 5 wherein automatically defining the nominal cutting line is performed so as to exclude unclassified objects.

11. The method as recited in claim 5 wherein the defining specific classification features includes defining a range of values for at least one of the specific classification features.

12. The method as recited in claim 5 further comprising excluding from the nominal cutting line objects, identified by the comparing the existing object features to the defined specific classification features, that border on an edge of the image detail or that are only partially visible in the image detail.

13. The method as recited in claim 3 further comprising removing a specific unwanted object of the at least one object from the binary image using image analysis morphology, the unwanted object being not designated for microdissection.

14. The method as recited in claim 1 wherein the electronic image is either a grayscale image or a color image.

15. The method as recited in claim 1 wherein the at least one object includes a plurality of objects disposed in close proximity to one another, and further comprising combining the plurality of objects into a cluster, and wherein the automatically defining a nominal cutting line is performed so as to define a single shared nominal cutting line surrounding the cluster.

16. The method as recited in claim 15 further comprising separately cutting out at least one region enclosed by the cluster and not belonging to the cluster.

17. The method as recited in claim 1 further comprising:
applying a mathematical transformation so as to automatically map the nominal cutting line onto a laser cutting line; and
converting the laser cutting line into the relative motion between the laser beam and the specimen so as to provide a laser cut.

18. The method as recited in claim 17 further comprising initiating, by a user or automatically, the relative motion between the laser beam and the specimen.

19. The method as recited in claim 17, wherein:
the contour is an outer contour of the at least one object;
the automatically calculating includes determining the outer contour of the at least one object using image analysis; and
the automatically defining includes converting the outer contour into a numerical code specifying the automatically defined nominal cutting line.

20. The method as recited in claim 19 wherein the numerical code is a Freeman code or a chain code.

21. The method as recited in claim 1 further comprising performing an automatic shading correction including:
recording an empty image without a specimen;
storing the empty image as a shading correction image; and
applying an offset correction to the captured electronic image using the shading correction image.

22. The method as recited in claim 1 further comprising providing a defined clearance distance in the specimen so as to prevent a neighboring object from being sliced through.

23. The method as recited in claim 1 further comprising superimposing, by an imaging device, the nominal cutting line onto the electronic image so as to control results of the cutting out.

24. The method as recited in claim 1 further comprising:
applying a mathematical transformation so as to automatically map the nominal cutting line onto a laser cutting line; and
scaling the laser cutting line as a function of the image magnification.

25. The method as recited in claim 1 further comprising:
applying a mathematical transformation so as to automatically map the nominal cutting line onto a laser cutting line; and
setting a defined clearance distance of the laser cutting line from the at least one so as to protect the object from damage caused by laser irradiation.

26. The method as recited in claim 1 further comprising modifying the nominal cutting line so as to compensate for imprecise repositioning of the microscope stage.

\* \* \* \* \*